United States Patent [19]

Santilli et al.

[11] Patent Number: 5,288,871
[45] Date of Patent: Feb. 22, 1994

[54] ANTIOSTEOPOROTIC IMIDAZO[4,5-C]PYRIDINES

[75] Inventors: Arthur A. Santilli, Havertown; Susan M. Andrews, Newtown; Donald P. Strike, St. Davids, all of Pa.

[73] Assignee: American Home Products Corporation, Madison, N.J.

[21] Appl. No.: 101,153

[22] Filed: Aug. 2, 1993

[51] Int. Cl.$^5$ .......................................... C07D 471/04
[52] U.S. Cl. .................................................. 546/118
[58] Field of Search ........................ 546/118; 514/303

[56] References Cited

U.S. PATENT DOCUMENTS 5,081,253  1/1992  Santilli et al. ...................... 546/118

Primary Examiner—C. Warren Ivy
Assistant Examiner—D. Margaret M. Mach
Attorney, Agent, or Firm—Walter Patton

[57] ABSTRACT

This invention relates to 2-substituted-imidazo[4,5-c]pyridines, to the process for their preparation, to pharmaceutical compositions containing said 2-substituted-imidazo]4,5-c]pyridines and to the use of said 2-substituted-imidazo[4,5-c]pyridines for modifying the balance between bone production and bone resorption in a host animal, including man.

20 Claims, No Drawings

ANTIOSTEOPOROTIC IMIDAZO[4,5-C]PYRIDINES

This invention relates to 2-substituted-imidazo[4,5-c]pyridines, to the process for their preparation, to pharmaceutical compositions containing said 2-substituted-imidazo[4,5-c]pyridines and to the use of said 2-substituted-imidazo[4,5-c]pyridines for modifying the balance between bone production and bone resorption in a host animal, including man.

BACKGROUND OF THE INVENTION

Osteoporosis is a skeletal disorder which is evidenced by an increase in fracture incidence resulting from a decrease in bone density. In fact, both the bone mineral (calcium phosphate called "hydroxyapatite") and the bone matrix (major protein called "collagen") are lost. This condition may begin to occur in humans as early as age 30. In general, the process is more rapid in postmenopausal women than in men. However, after age 80 there is no sex difference in the incidence of osteoporosis. In the course of 10 to 20 years of bone loss there may be symptoms of back pain and X-ray evidence of deformation of the spine. At older ages, the brittleness of the bones becomes evident by the ease with which the proximal femur ("hip") fractures. Osteoporosis is the most common cause of fractures in people over age 45.

Although the cause of osteoporosis is poorly understood, it is believed that there is an imbalance between bone production and bone resorption (bone breakdown). Bone remains a dynamic tissue throughout the life of an animal. That is, new bone is continuously being formed and old bone is continuously being resorbed. However, in animals suffering from an osteoporotic condition, net bone resorption exceeds bone formation.

A survey indicates that in the United States there may be fifteen to twenty million people afflicted with osteoporosis [W. A. Peck (Chairman), NIH Osteoporosis Consensus Conference, J. Am. Med. Assoc., 10, 252:799–802 (1984)]. Various types of osteoporosis are designated according to special conditions believed to be causative: senile (aging); post-menopausal (female loss of estrogenesis); disuse (chronic immobilization); steroid (long term steroid treatment as in arthritis); hypercalcemia of malignancy. Osteoporosis may also be manifested in dental problems since the mandible appears to lose mass more rapidly than any other bone. Thus, periodontal disease involving a loosening of the adult teeth may be an early sign of osteoporosis.

The mechanism of bone loss is at present poorly understood. Moreover, the present methods of treatment are generally unsatisfactory. These include anabolic agents, various drugs containing phosphorous, Vitamin D, calcium salts, fluorides and calcitonin.

Estrogen replacement therapy has been the therapy of choice for osteoporosis in post-menopausal women. Physical therapy is another method currently used to treat osteoporosis since immobilization can cause osteoporosis at any age. Thus, many physicians believe that exercise and physical therapy can prevent the progression of the disease in elderly patients. However, physical therapy can be harmful for patients with fractures and, moreover, overstrenuous exercise can cause fractures in patients with severe osteoporosis.

Other treatments include the administration of a fluoride salt such as sodium fluoride which has been shown to promote bone growth clinically, apparently by stimulating collagen synthesis. However, a serious side effect is poorly calcified, irregular bone growth. Another treatment involves infusion of calcium and Vitamin D to counteract the deficiency of calcium or impaired absorption of calcium which is symptomatic in some elderly patients. There is, however, no evidence that a higher intake of calcium will prevent osteoporosis or increase bone mass in adults.

The most promising therapeutic approach to the treatment of osteoporosis is the administration of agents which have been designed to modify the balance between the rate of bone production and the rate of bone resorption in such a manner that the ratio of the former to the latter is increased, resulting in no net bone loss. After the previously occurred bone losses have been restored, a steady state is reached where the rate of bone production and rate of bone resorption are equal. Such a modification may be effected by stimulating the physiological mechanism of bone deposition, i.e., bone formation, or by retarding the mechanism of bone resorption, or both. Drugs presently in use or in the experimental stages for accomplishing these purposes include phosphonates, calcitonin and mithramycin. However, all of these drugs suffer serious drawbacks.

Mithramycin, an antibiotic, has anti-tumor activity together with hypocalcemic activity, causing a reduction of serum calcium which in turn is believed to be indicative of a decrease in the relative of bone resorption—i.e., bone resorption relative to bone production. Side effects, however, include renal and hepatic toxicity as well as nausea. Likewise, the organic phosphonates have side effects which include extra-skeletal calcification, hypotension and renal failure. Calcitonin presents an immunological problem because it is commonly derived from a non-human source. Thus, none of the foregoing agents are at present suitable for use alone in the treatment of osteoporosis.

PRIOR ART

The closest prior art is U.S. Pat. No. 5,081,253, Japanese Patent J6 3146-883-A and International Patent Applications WO 89/03829; WO 89/03830 and WO 89/03833.

SUMMARY OF THE INVENTION

This invention relates to novel 2-substituted-imidazo[4,5-c]pyridine derivatives useful in inhibiting bone resorption and having the formula (I) or its tautomer having the formula (I')

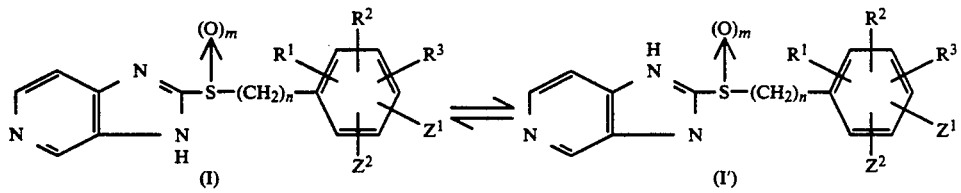

wherein $R^1$, $R^2$ and $R^3$ are independently selected from the group consisting of hydrogen, lower alkyl containing 1 to 6 carbon atoms, hydroxy, lower alkyloxy containing 1 to 6 carbon atoms, halogen, trifluoromethyl, trifluoromethoxy, nitro, cyano, phenoxy, benzyloxy, aminoacetyl, $-S(O)_p-CH_3$ or any two adjacent groups are joined to form methylenedioxy; $Z^1$ and $Z^2$ are independently selected from the group consisting of

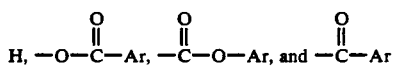

wherein Ar is phenyl; alkyl, alkoxy or hydroxy substituted phenyl; or thienyl, wherein alkyl and alkoxy contain 1 to 6 carbon atoms with the proviso that $Z^1$ and $Z^2$ are not both hydrogen; m is 0 to 2; n is 1 to 3; p is 0 to 2, and the pharmaceutically acceptable salts and hydrates thereof.

Preferred compounds of the present invention are those of formula (II)

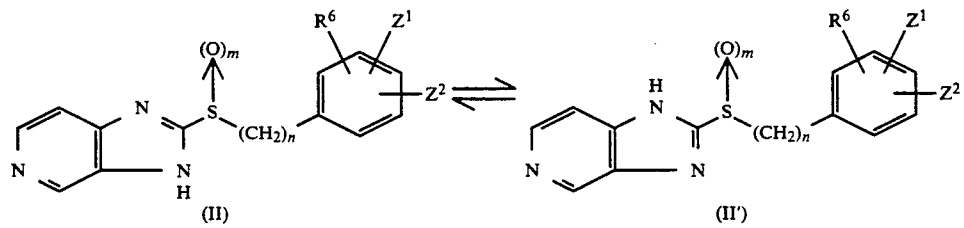

wherein $R^6$ is hydrogen, hydroxy, lower alkyloxy containing 1 to 6 carbon atoms; $Z^1$ and $Z^2$ are independently selected from the group consisting of

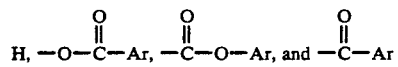

wherein Ar is phenyl; alkyl, alkoxy or hydroxy substituted phenyl; or thienyl, wherein alkyl and alkoxy contain 1 to 6 carbon atoms with the proviso that $Z^1$ and $Z^2$ are not both hydrogen; m is 0 to 2; n is 1 to 2, and the pharmaceutically acceptable salts and hydrates thereof.

Further preferred compounds of the present invention are those of formula (III)

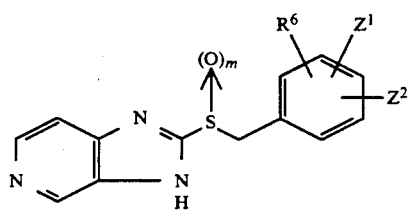

wherein $R^6$ is hydrogen, hydroxy, methoxy; $Z^1$ and $Z^2$ are independently selected from the group consisting of

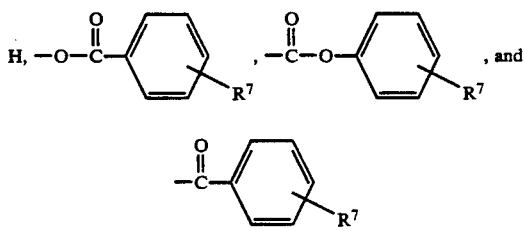

wherein $R^7$ is hydrogen, hydroxy, methoxy with the proviso that $Z^1$ and $Z^2$ are not both hydrogen; m is 0 to 2; and the pharmaceutically acceptable salts and hydrates thereof.

The most preferred compounds of the present invention are designated

3-[(1H-imidazo[4,5-c]pyridin-2-ylthio)methyl]phenol benzoate (ester) hemihydrate;
3-[(1H-imidazo[4,5-c]pyridin-2-ylsulfinyl)methyl]-phenol benzoate (ester) quarter hydrate;
3-[(1H-imidazo[4,5-c]pyridin-2-ylsulfinyl)methyl]-phenol;
4-[(1H-imidazo[4,5-c]pyridin-2-ylthio)methyl]-2-methoxyphenol benzoate (ester) hemihydrate;
4-[(1H-imidazo[4,5-c]pyridin-2-ylsulfinyl)methyl]-2-methoxyphenyl benzoate (ester) quarter hydrate;
4-(3H-imidazo[4,5-c]pyridin-2-ylthiomethyl)benzene-1,2-diol dibenzoate (ester) quarter hydrate;
3-methoxybenzoic acid 3-(1H-imidazo[4,5-c]pyridin-2-ylthiomethyl)-phenyl ester quarter hydrate;
3-methoxy-benzoic acid 3-(1H-imidazo[4,5-c]pyridine-2-sulfinylmethyl)-phenyl ester one-third hydrate;
3-(1H-imidazo[4,5-c]pyridin-2-ylthiomethyl)-benzoic acid phenyl ester quarter hydrate;
3-(1H-imidazo[4,5-c]pyridine-2-sulfinylmethyl)-benzoic acid phenyl ester one-third hydrate;
[3-(1H-imidazo[4,5-c]pyridin-2-ylthiomethyl)-phenyl]-phenyl methanone quarter hydrate;
[3-(1H-imidazo[4,5-c]pyridine-2-sulfinylmethyl)-phenyl]-phenyl-methanone one-third hydrate;
2-[(1H-imidazo[4,5-c]pyridin-2-ylthio)methyl]phenol benzoate (ester);

4-[(1H-imidazo[4,5-c]pyridin-2-ylthio)methyl]-phenol benzoate (ester);

5-(3H-imidazo[4,5-c]pyridin-2-ylthiomethyl)benzene-1,3-diol dibenzoate (ester);

benzoic acid 3-hydroxy-5-(1H-imidazo[4,5-c]pyridin-2-ylthiomethyl)phenyl ester quarter hydrate; and the pharmaceutically acceptable salts and hydrates thereof.

The sulfoxides of this invention possess an asymmetric sulfur atom and thus are made as racemic mixtures. It is to be understood that the definition of the sulfoxides of Formula (I) and (I') encompasses all possible stereoisomers, R and S enantiomers, tautomers and mixtures thereof which possess the activity discussed below. In particular, it encompasses racemic modifications and any optical isomers which possess the indicated activity.

It is another object of this invention to provide an improved process for the production of 2-substituted-imidazo[4,5-c]pyridines according to the following Reaction Scheme.

REACTION SCHEME

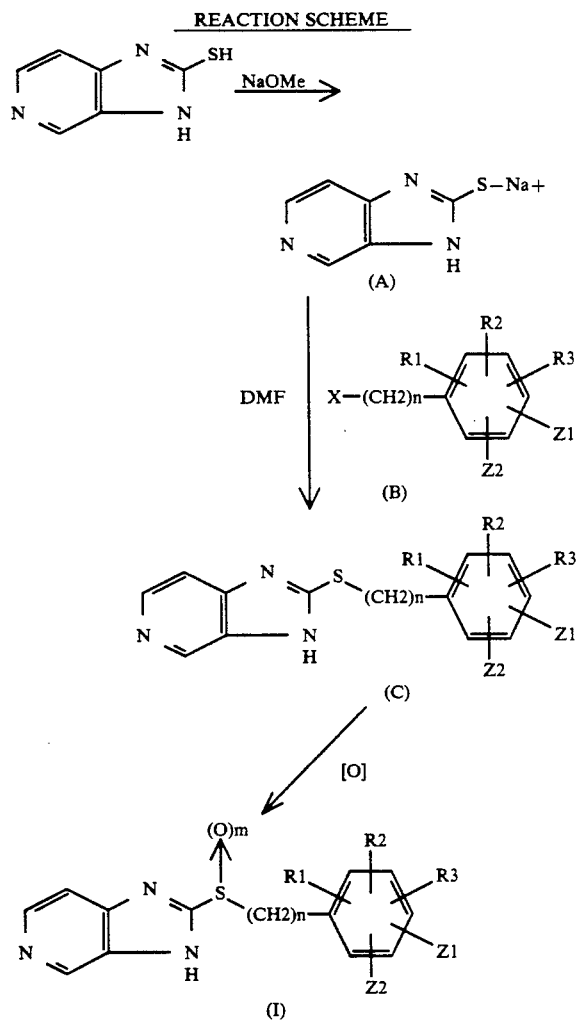

wherein $R^1$, $R^2$, $R^3$, $Z^1$, $Z^2$, m and n are as defined above and X is Cl, Br, I or tosyl.

The compounds of this invention are generally prepared sequentially by first forming the sodium salt of 2-mercaptoimidazo[4,5-c]pyridine (A) with sodium methoxide. Treatment of (A) in DMF with an equivalent of a suitably substituted alkylating agent (B), affords the corresponding sulfide derivative (C). Finally, oxidation of (C) with an equivalent of an oxidizing agent such as selenium dioxide/hydrogen peroxide, m-chloroperoxybenzoic acid or peracetic acid at reduced temperature affords the desired sulfoxide (I).

It is also another object of this invention to provide a method whereby a host animal, including man, suffering from osteoporosis is treated in order to modify the balance between the rates of bone deposition and bone resorption in said host animal whereby the ratio of the latter to the former is reduced.

Still another object of this invention is to provide a process for the treatment of a host animal in order to prevent the deterioration of existing healthy bone tissues in said host animal. It is possible that these agents could also be of utility in the treatment of hypercalcemia of malignancy, Paget's disease, hyperparathyroidism, immobilization, glucocorticoid-induced osteopenia, and the arthritides.

It is a further object of this invention to provide a process for the treatment of periodontal disease.

DETAILED DESCRIPTION OF THE INVENTION

The compounds of formula (I) of this invention are used alone or in combination with pharmacologically acceptable carriers, the proportion of which is determined by the solubility and chemical nature of the compound, chosen route of administration and standard medical practice. For example, they are administered orally in the form of capsules, tablets, suspensions or solutions or by oral topical administration or they may be injected parenterally. Capsules and tablets are the preferred mode of administration. For parenteral administration they can be used in the form of a sterile solution containing other solutes, for example enough saline or glucose to make the solution isotonic.

The capsule and tablet compositions contain the active ingredient in admixture with non-toxic pharmaceutical excipients known to be suitable in the manufacture of capsules and tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula (I) contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil for example, arachis oil, olive oil, sesame oil, or coconut oil, or in mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula (I) will vary with the form of administration and the particular compound chosen. Furthermore, it will vary with the particular host as well as the age, weight and condition of the host under treatment, as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective amount of the compounds for oral administration can usually range from about 200 mg to 1200 mg/day in single or divided doses although, as aforementioned, variations will occur. However, a dosage level that is in the range of from about 500 mg to 900 mg/day in single or divided doses is employed most desirably for oral administration in order to achieve effective results.

The following examples are provided to illustrate the methods of preparation and testing of the compounds of the present invention. These examples are not meant to be considered, in any way, as limitations of the breadth and scope of the present invention. The temperatures expressed in these examples are in degrees centigrade.

EXAMPLE 1

3-Methylphenyl benzoate

To a chilled (0°–5° C.) solution of 5.0 g (0.046 mol) of m-cresol in 20 mL of methylene chloride containing 5.16 g (0.051 mol) of triethylamine was added dropwise a solution containing 6.47 g (0.046 mol) of benzoyl chloride in 20 mL of methylene chloride. A precipitate formed upon addition. The reaction mixture was stirred several hours at room temperature and was then filtered. The filtrate was washed with water (25 mL) and then with brine (25 mL). The organic phase was removed and dried over magnesium sulfate, filtered and evaporated to dryness in a rotary evaporator. The crude product amounted to 9.66 g. An analytical sample (m.p. 51°–54° C.) was obtained by recrystallization from petroleum ether.

Elemental analysis for $C_{14}H_{12}O_2$: Calc'd: C, 79.23; H, 5.70; Found: C, 79.05; H, 5.67.

EXAMPLE 2

3-(Bromomethyl)phenyl benzoate

To a solution of 20.83 g (0.098 mol) of 3-methylphenyl benzoate in 280 mL of carbon tetrachloride was added a catalytic amount of benzoyl peroxide, followed by 20.96 g (0.118 mol) of N-bromosuccinimide. The reaction mixture was stirred and heated under reflux overnight. After cooling to room temperature, the solid material was filtered off. The filtrate was washed with 100 mL of water. The organic phase was removed and dried over magnesium sulfate, filtered and evaporated to dryness in a rotary evaporator. The crude product (31.3 g) was purified by HPLC to give 20.61 g and was used directly in the next step.

EXAMPLE 3

3-[(1H-Imidazo[4,5-c]pyridin-2-ylthio)methyl]phenol benzoate (ester) Hemihydrate To a solution of 1.62 g (0.07 g atom) of sodium in 340 mL of methanol was added 9.69 g (0.064 mol) of 2-mercapto-1H-imidazo[4,5-c]pyridine. After stirring for 30 minutes at room temperature, the reaction mixture was evaporated to dryness in a rotary evaporator. To the residue was added 145 mL of dimethylformamide. To the resulting solution was added dropwise 18.69 g (0.064 mol) of 3-(Bromomethyl)phenyl benzoate in 100 mL of dimethylformamide. The reaction mixture was stirred overnight at room temperature and was then poured into 500 mL of chilled water. The reaction mixture was extracted with methylene chloride (3×300 mL). The combined organic phase was dried over magnesium sulfate, filtered and evaporated to dryness. The residual oil was triturated with hot chloroform. The precipitate that formed was collected by filtration and amounted to 14.65 g. An analytical sample (m.p. 136°–139° C.) was obtained by recrystallization from ethyl acetate.

Elemental analysis for $C_{20}H_{15}N_3O_2S \cdot \frac{1}{2}H_2O$; Calc'd: C, 64.85; H, 4.35; N, 11.34; Found: C, 65.05; H, 4.16; N, 11.30.

EXAMPLE 4

3-[(1H-Imidazo[4,5-c]pyridin-2-ylsulfinyl)methyl]-phenol benzoate (ester) Quarter Hydrate To a solution of 2.73 g (0.0076 mol) of 3-[(1H-imidazo[4,5-c]pyridin-2-ylthio)methyl]-phenol benzoate (ester) in 70 mL of ethyl acetate and 10 mL of methanol was added dropwise a solution containing 2.69 g (0.011 mol) of peracetic acid in 5 mL of ethyl acetate. The reaction mixture was stirred several hours at room temperature and was then evaporated to near dryness in a rotary evaporator. The crude product (4.3 g) when subjected to HPLC gave pure product (m.p. 156°–159° C.).

Elemental analysis for $C_{20}H_{15}N_3O_3S \cdot \frac{1}{4} H_2O$: Calc'd: C, 62.89; H, 4.09; N, 11.00; Found: C, 62.81; H, 3.92; N, 10.71.

EXAMPLE 5

3-[(1H-Imidazo[4,5-c]pyridin-2-ylsulfinyl)methyl]-phenol

3-[(1H-Imidazo[4,5-c]pyridin-2-ylsulfinyl)methyl]-phenol benzoate (ester) (2.65 g, 0.007 mol) was dissolved in 260 mL of ammonium hydroxide. The reaction mixture was stirred for 1 ½ hours at room temperature. The ammonia was removed in a rotary evaporator and the reaction mixture was chilled in ice. The precipitate that formed was collected on a filter and rinsed with water giving 1.70 g of product. (m.p. 224°–227° C.) (dec.).

Elemental analysis for $C_{13}H_{11}N_3O_2S$: Calc'd: C, 57.13; H, 4.06; N, 15.37; Found: C, 56.99; H, 4.07; N, 14.85.

EXAMPLE 6

2-Methoxy-4-methylphenyl benzoate

The synthesis of this compound proceeded in the same fashion as in Example 1 using 27.63 g (0.20 mol) of 2-methoxy-4-methyl phenol, 22.26 g (0.22 mol) of triethylamine and 28.11 g (0.20 mol) of benzoyl chloride. The product amounted to 46.78 g, m.p. 73°–75° C.

Elemental analysis for $C_{15}H_{14}O_3$: Calc'd: C, 74.36; H, 5.82; Found C, 74.08; H, 5.90.

EXAMPLE 7

4-Bromomethyl-2-methoxyphenyl benzoate

The synthesis of this compound proceeded in the same fashion as in Example 2 using 22.59 g (0.093 mol) of 2-methoxy-4-methylphenyl benzoate, a catalytic amount of benzoyl peroxide and 19.92 g (0.11 mol) of N-bromosuccinimide. The crude product (29.36 g) was purified by HPLC to give 8.95 g, m.p. 86°–88° C.

Elemental analysis for $C_{15}H_{13}BrO_3$: Calc'd: C, 56.10; H, 4.08; Found: C, 55.94; H, 4.23.

EXAMPLE 8

4-[(1H-Imidazo[4,5-c]pyridin-2-ylthio)methyl]-2-methoxyphenol benzoate (ester) Hemihydrate The synthesis of this compound proceeded in the same fashion as in Example 3 using 4.08 g (0.027 mol) of 2-mercapto-1H-imidazo[4,5-c]pyridine, 0.68 g (0.03 g atom) of sodium and 8.67 g (0.027 mol) of 4-bromomethyl-2-methoxyphenyl benzoate. Recrystallization of the crude product from methanol/chloroform gave 6.03 g, m.p. 215°–218° C.

Elemental analysis for $C_{21}H_{17}N_3O_3S \cdot \frac{1}{2} H_2O$: Calc'd: C, 62.98; H, 4.53; N, 10.49; Found: C, 62.88; H, 4.44; N, 10.22.

EXAMPLE 9

4-[(1H-Imidazo[4,5-c]pyridin-2-ylsulfinyl)methyl]-2-methoxyphenyl benzoate (ester) Quarter Hydrate 4-[(1H-Imidazo[4,5-c]pyridin-2-ylthio)methyl]-2-methoxyphenyl benzoate (ester) (3.7 g, 0.0094 mol) was dissolved in 75 mL of methanol and 200 mL of chloroform with heating. At room temperature, a solution of 2.25 g (0.0094 mol) of peracetic acid in 30 mL of methanol was added dropwise to the reaction mixture. The reaction mixture was stirred overnight at room temperature and then was evaporated to dryness in a rotary evaporator. The crude product amounted to 5.56 g and was purified by HPLC. An analytical sample, m.p. 164°–167° C., was obtained by recrystallization from methylene chloride.

Elemental analysis for $C_{21}H_{17}N_3O_4S \cdot \frac{1}{4} H_2O$: Calc'd: C, 61.22; H, 4.28; N, 10.20; Found: C, 61.33; H, 4.06; N, 10.41

EXAMPLE 10

4-Methyl-benzene-1,2-diol dibenzoate

The synthesis of this compound proceeded in the same fashion as in Example 1 using 12.41 g (0.10 mol) of 4-methylcatechol, 22.26 g (0.22 mol) of triethylamine and 28.11 g (0.20 mol) of benzoyl chloride. The crude material (32.88 g) when subjected to HPLC gave pure product, m.p. 65°–67° C.

Elemental analysis for $C_{21}H_{16}O_4$: Calc'd: C, 75.89; H, 4.85; Found: C, 75.58; H, 4.81

EXAMPLE 11

4-Bromomethyl-benzene-1,2-diol dibenzoate

To a solution of 19.94 g (0.06 mol) of 4-methyl-benzene-1,2-diol dibenzoate in 350 mL of carbon tetrachloride was added a catalytic amount of 2,2'-azobisisobutyronitrile, followed by 10.68 g (0.06 mol) of N-bromosuccinimide. The reaction mixture was stirred at room temperature for several days and was then filtered. The filtrate was dried over $MgSO_4$, filtered and evaporated to dryness in a rotary evaporator. Purification of the crude material (24.76 g) by HPLC gave 7.05 g of product which was used directly in the next step.

EXAMPLE 12

4-(3H-Imidazo[4,5-c]pyridin-2-ylthiomethyl)benzene-1,2-diol dibenzoate (ester) Quarter Hydrate The synthesis of this compound proceed in the same fashion as in Example 3 using 1.77 g (0.0117 mol) of 2-mercapto-1H-imidazo[4,5-c]pyridine, 0.30 g (0.0129 g atom) of sodium and 4.81 g (0.0117 mol) of 4-bromomethyl-benzene-1,2-diol dibenzoate. Recrystallization of the precipitate from chloroform gave 2.10 g of pure product, m.p. 173°–175° C.

Elemental analysis for $C_{27}H_{19}N_3O_4S \cdot \frac{1}{4} H_2O$: Calc'd: C, 66.72; H, 4.04; N, 8.65; Found: C, 66.71; H, 3.93; N, 8.43.

EXAMPLE 13

3-Methoxy-benzoic acid 3-methyl-phenyl ester One-tenth Hydrate

The synthesis of this compound proceeded in the same fashion as in Example 1 using 16.22 g (0.15 mol) of m-cresol, 16.70 g (0.165 mol) of triethylamine and 25.59 g (0.15 mol) of m-anisoyl chloride. The product amounted to 34.01 g.

Elemental analysis for $C_{15}H_{14}H_3 \cdot 1/10 H_2O$: Calc'd: C, 73.81; H, 5.86; Found: C, 73.67; H, 5.80.

EXAMPLE 14

3-Methoxy-benzoic acid 3-bromomethyl-phenyl ester Quarter Hydrate

The synthesis of this compound proceeded in the same fashion as in Example 11 using 33.51 g (0.138 mol) of 3-methoxy-benzoic acid 3-methyl-phenyl ester, a catalytic amount of 2,2'-azobisisobutyronitrile and 24.62 g (0.138 mol) of N-bromosuccinimide. The crude product (46.40 g) was purified by HPLC to give 26.53 g, m.p. 55°–58° C.

Elemental analysis for $C_{15}H_{13}BrO_3 \cdot \frac{1}{4} H_2O$: Calc'd: C, 55.32; H, 4.18; Found: C, 54.98; H, 3.94.

EXAMPLE 15

3-Methoxybenzoic acid 3-(1H-imidazo[4,5-c]pyridin-2-ylthiomethyl)-phenyl ester Quarter Hydrate To a solution of 1.01 g (0.044 g atom) of sodium in 225 mL of methanol was added 6.04 g (0.04 mol) of 2-mercapto-1H-imidazo[4,5-c]pyridine. After stirring for 20 minutes at room temperature, the reaction mixture was evaporated to dryness in a rotary evaporator. To the residue was added 150 mL of dimethylformamide followed by the portionwise addition of 12.85 g (0.04 mol) of 3-methoxy-benzoic acid 3-bromomethyl-phenyl ester. The reaction mixture was stirred overnight at room temperature and was then poured into 500 mL of chilled water. The product was removed by filtration and amounted to 9.66 g. An analytical sample (m.p. 149°–151° C.) was obtained by recrystallization from ethyl acetate.

Elemental analysis for $C_{21}H_{17}N_3O_3S \cdot \frac{1}{4} H_2O$: Calc'd: C, 63.70; H, 4.46; N, 10.61; Found: C, 63.72; H, 4.37; N, 10.77.

EXAMPLE 16

3-Methoxy-benzoic acid 3-(1H-imidazo[4,5-c]pyridine-2-sulfinylmethyl)-phenyl ester One-third Hydrate To a chilled (0°–5° C.) solution of 4.53 g (0.0116 mol) of 3-methoxy-benzoic acid 3-(1H-imidazo[4,5-c]pyridin-2-ylthiomethyl)-phenyl ester in 135 mL of ethyl acetate and 15 mL of methanol was added dropwise a solution containing 2.74 g (0.0116 mol) or peracetic acid in 10 mL of methanol. The reaction mixture was stirred at room temperature overnight. The product (3.2 g) was collected by filtration. An analytical sample, m.p. 163°–165° C., was obtained by recrystallization from chloroform.

Elemental analysis for $C_{21}H_{17}N_3O_4S.\frac{1}{3} H_2O$: Calc'd: C, 61.00; H, 4.31; N, 10.16; Found: C, 60.97; H, 4.14; N, 10.16.

EXAMPLE 17

3-Methylbenzoic acid phenyl ester

A solution of 23.19 g (0.15 mol) of m-toluoyl chloride in 70 mL of methylene chloride was added dropwise to a solution containing 14.12 g (0.15 mol) of phenol and 16.7 g (0.165 mol) of triethylamine in 70 mL of methylene chloride at ice bath temperature. A precipitate formed upon addition. The reaction mixture was stirred overnight at room temperature and was then filtered. The filtrate was washed successively by water (100 mL) and then by brine (75 mL) The organic layer was removed and dried over magnesium sulfate, filtered and evaporated in a rotary evaporator. The clear liquid product amounted to 29.91 g.

Elemental analysis for $C_{14}H_{12}O_2$: Calc'd: C, 79.22; H, 5.70; Found: C, 79.06; H, 5.56.

EXAMPLE 18

3-(Bromomethyl)benzoic acid phenyl ester One-tenth Hydrate

To a solution of 21.22 g (0.10 mol) phenyl 3-methylbenzoate in 640 mL of carbon tetrachloride was added to a catalytic amount of 2,2'-azobisisobutyronitrile, followed by 17.8 g (0.10 mol) of N-bromosuccinimide. The reaction mixture was stirred several hours at room temperature and then heated under reflux for 3 hours. After cooling to room temperature, the solid material was filtered and the filtrate was poured into water (200 mL). The organic layer was removed and dried over magnesium sulfate, filtered and evaporated in a rotary evaporator. Purification of the crude material by HPLC gave 14.28 g of product (m.p. 60°–63° C.).

Elemental analysis for $C_{14}H_{11}BrO_2.1/10 \; H_2O$: Calc'd: C, 57.40; H, 3.85; Found: C, 57.01; H, 3.85.

EXAMPLE 19

3-(1H-Imadazo[4,5-c]pyridin-2-ylthiomethyl)-benzoic acid phenyl ester Quarter Hydrate The synthesis of this compound proceeded in the same fashion as in Example 3 using 6.66 g (0.0441 mol) of 2-mercapto-1H-imidazo[4,5-c]pyridine, 1.12 g (0.0485 g atom) of sodium and 14.13 g (0.0485 mol) of 3-(bromomethyl)benzoic acid phenyl ester. Recrystallization of the precipitate from ethyl acetate gave 10.20 g of product, m.p. 129°–132° C.

Elemental analysis for $C_{20}H_{15}N_3O_2S.\frac{1}{4}H_2O$; Calc'd: C, 65.64; H, 4.27; N, 11.48; Found: C, 65.75; H, 4.26; N, 11.44.

EXAMPLE 20

3-(1H-Imidazo[4,5-c]pyridine-2-sulfinylmethyl)-benzoic acid phenyl ester One-third Hydrate The synthesis of this compound proceeded in the same fashion as in Example 16 using 3.94 g (0.011 mol) of 3-(1H-imidazo[4,5-c]pyridin-2-ylthiomethyl)-benzoic acid phenyl ester and 2.58 g (0.011 mol) of peracetic acid. The filtered precipitate amounted to 3.0 g. An analytical sample, m.p. 174°–176° C., was obtained by recrystallization from ethanol.

Elemental analysis for $C_{20}H_{15}N_3O_3S.\frac{1}{3} H_2O$; Calc'd: C, 62.65; H, 4.12; N, 10.96; Found: C, 62.26; H, 4.21; N, 10.77.

EXAMPLE 21

[3-(1H-Imidazo[4,5-c]pyridin-2-ylthiomethyl)-phenyl]-phenyl methanone Quarter Hydrate To a solution of 0.46 g (0.02 g atom) of sodium in 120 mL of methanol was added 2.74 g (0.018 mol) of 2-mercapto-1H-imidazo[4,5-c]pyridine. After stirring at room temperature for 30 minutes, 5.0 g (0.018 mol) of 3-bromomethyl-benzophenone was added portionwise. The reaction mixture was stirred overnight at room temperature and was then evaporated to dryness in a rotary evaporator. Water (75 mL) was added to the residue and the resulting material was filtered. Purification by HPLC gave a product which upon recrystallization from ethanol amounted to 9.2 g (m.p. 149°–151° C.).

Elemental analysis for $C_{20}H_{15}N_3OS.\frac{1}{4} H_2O$. Calc'd: C, 68.65; H, 4.47; N, 12.01; Found: C, 68.34; H, 4.54; N, 12.04.

EXAMPLE 22

[3-(1H-Imidazo[4,5-c]pyridine-2-sulfinylmethyl)-phenyl]-phenyl-methanone One-third Hydrate A solution of 1.78 g (0.0075 mol) of peracetic acid in 5 mL of ethanol was added dropwise to a solution containing 2.58 g (0.0075 mol) of [3-(1H-imidazo[4,5-c]pyridin-2-ylthiomethyl)-phenyl]-phenyl methanone in 30 mL of ethanol at ice bath temperature. The reaction mixture was stirred several hours at room temperature and was then evaporated to near dryness in a rotary evaporator. The crude material was dissolved in methylene chloride and poured into water. The organic layer was removed and dried over magnesium sulfate, filtered and evaporated to dryness. The crude product (3.6 g) when subjected to HLPC gave 1.42 g of pure product, m.p. 142°–145° C. (dec.).

Elemental analysis for $C_{20}H_{15}N_3O_2S.\frac{1}{3} H_2O$: Calc'd: C, 65.38; N, 4.30; N, 11.44; Found: C, 65.48; H, 4.40; N, 10.98.

EXAMPLE 23

2-Methylphenyl benzoate One-tenth Hydrate

The synthesis of this compound proceeded in the same fashion as in Example 1 using 21.63 g (0.20 mol) of o-cresol, 22.26 g (0.22 mol) of triethylamine and 28.11 g (0.20 mol) of benzoyl chloride. The product amounted to 38.79 g.

Elemental analysis for $C_{14}H_{12}O_2.1/10 \; H_2O$: Calc'd: C, 78.55; H, 5.75; Found: C, 78.66; H, 5.84.

EXAMPLE 24

2-(Bromomethyl)phenyl benzoate Quarter Hydrate

The synthesis of this compound proceeded in the same fashion as in Example 11 using 21.22 g (0.10 mol) of 2-methylphenyl benzoate, a catalytic amount of 2,2'-azobisisobutyronitrile and 17.80 g (0.10 mol) of N-bromosuccinimide. The crude material (37.12 g) was purified by HPLC to give 20.8 g. An analytical sample, m.p. 77°–79° C., was obtained by recrystallization from hexane.

Elemental analysis for $C_{14}H_{11}BrO_2 \cdot \frac{1}{4} H_2O$: Calc'd: C, 56.87; H, 3.92; Found: C, 56.75; H, 3.89.

EXAMPLE 25

2-[(1H-Imidazo[4,5-c]pyridin-2-ylthio)methyl]phenol benzoate (ester)

The synthesis of this compound proceeded in the same fashion as in Example 3 using 6.79 g (0.045 mol) of 2-mercapto-1H-imidazo[4,5-c]pyridine, 1.14 g (0.0495 g atom) of sodium and 13.09 g (0.045 mol) of 2-(bromomethyl)phenyl benzoate. Purification of the crude material (12.75 g) by HPLC gave a product which on recrystallization from ethyl acetate had a m.p. 129°–132° C.

Elemental analysis for $C_{20}H_{15}N_3O_2S$: Calc'd: C, 66.47; H, 4.18; N, 11.63; Found: C, 66.25; H, 4.13; N, 11.60.

EXAMPLE 26

4-Methylphenyl benzoate

The synthesis of this compound proceeded in the same fashion as in Example 1 using 21.63 g (0.20 mol) of p-cresol, 22.26 g (0.22 mol) of triethylamine and 28.11 g (0.20 mol) of benzoyl chloride. The product amounted to 39.95 g, m.p. 66°–69° C.

Elemental analysis for $C_{14}H_{12}O_2$: Calc'd: C, 79.23; H, 5.70; Found: C, 79.48; H, 5.68.

EXAMPLE 27

4-(Bromomethyl)phenyl benzoate One-tenth Hydrate

The synthesis of this compound proceeded in the same fashion as in Example 11 using 21.22 g (0.10 mol) of 4-methylphenyl benzoate, a catalytic amount of 2,2'-azobisisobutyronitrile and 17.80 g (0.10 mol) of N-bromosuccinimide. The crude material (32.0 g) was purified by HPLC to give 8.34 g of pure product, m.p. 96°–100° C.

Elemental analysis for $C_{14}H_{11}BrO_2 \cdot 1/10 H_2O$ Calc'd: C, 56.36; H, 3.99 Found: C, 55.96; H, 3.54

EXAMPLE 28

4-[(1H-Imidazo[4,5-c]pyridin-2-ylthio)methyl]-phenol benzoate (ester)

The synthesis of this compound proceeded in the same fashion as in Example 15 using 4.17 g (0.028 mol) of 2-mercapto-1H-imidazo[4,5-c]pyridine, 0.70 g (0.030 g atom) of sodium, and 8.04 g (0.028 mol) of 4-(bromomethyl)phenyl benzoate. The filtered precipitate (7.90 g) was recrystallized from methylene chloride to give 5.40 g of product, m.p. 171°–174° C.

Elemental analysis for $C_{20}H_{15}N_3O_2S$: Calc'd: C, 66.46; H, 4.18; N, 11.62; Found: C, 66.62; H, 4.34; N, 11.46.

EXAMPLE 29

5-Methyl-benzene-1,3-diol dibenzoate

The synthesis of this compound proceeded in the same fashion as in Example 1 using 1.42 g (0.01 mol) of orcinol monohydrate, 2.23 g (0.022 mol) of triethylamine and 2.81 g (0.02 mol) of benzoyl chloride. The product amounted to 2.78 g, m.p. 80°–83° C.

Elemental analysis for $C_{21}H_{16}O_4$: Calc'd: C, 75.89; H, 4.85; Found: C, 75.49; H, 5.04.

EXAMPLE 30

5-Bromomethyl-benzene-1,3-diol dibenzoate

The synthesis of this compound proceeded in the same fashion as in Example 11 using 24.93 g (0.075 mol) of 5-methyl-benzene-1,3-diol dibenzoate, a catalytic amount of 2,2'-azobisisobutyronitrile and 13.35 g (0.075 mol) of N-bromosuccinimide. Recrystallization of the crude material from ethyl acetate gave a product (m.p. 123°–126° C.) which was used directly in the next step.

EXAMPLE 31

5-(3H-Imidazo[4,5-c]pyridin-2-ylthiomethyl)benzene-1,3-diol dibenzoate (ester)

The synthesis of this compound proceeded in the same fashion as Example 15 using 1.66 g (0.011 mol) of 2-mercapto-1H-imidazo[4,5-c]pyridine, 0.28 g (0.012 g atom) of sodium and 4.51 g (0.011 mol) of 5-bromomethyl-benzene-1,3-diol dibenzoate. The crude material (4.2 g) when subjected to HPLC gave pure product (m.p. 209°–212° C.).

Elemental analysis for $C_{27}H_{19}N_3O_4S$: Calc'd: C, 67.35; H, 3.98; N, 8.73; Found: C, 67.09; H, 4.04; N, 8.61.

EXAMPLE 32

Benzoic acid 3-hydroxy-5-(1H-imidazo[4,5-c]pyridin-2-ylthiomethyl)phenyl ester Quarter Hydrate This compound was obtained as a by-product from the synthesis described in Example 31. The pure by-product (m.p. 139°–142° C.) was isolated by HPLC purification of the crude material.

Elemental analysis for $C_{20}H_{15}N_3O_3S \cdot \frac{1}{4} H_2O$: Calc'd: C, 62.89; H, 4.09; N, 11.00; Found: C, 62.53; H, 4.18; N, 11.01.

The useful osteoporotic activity of the compounds of formula (I) are demonstrated by standard pharmacological tests, for example, the test designted: *Bone Resorption Assay:* $^{45}Ca$ *Release from Rat Limb Bones.*

The purpose of this assay is to identify compounds that inhibit basal or stimulated bone resorption in culture.

The ability of 2-substituted-imidazo[4,5-c]pyridines to modify the process of bone resorption was evaluated essentially as described by L. G. Raisz, Bone resorption in tissue culture. Factors influencing the response to parathyroid hormone. (J. Clin. Invest. 44:103–116, 1965) and P. H. Stern et al, comparisons of fetal rat limb bones and neonatal mouse calvaria: Effects of parathyroid hormone and 1,25-dihydroxyvitamin $D_3$ (Calcif. Tissue Int. 35:172–176, 1983).

PROCEDURE

Limb Bone Preparation

Timed pregnant Sprague-Dawley CD® rats (Charles River) are administered 100 $\mu Ci$ $^{45}CaCl_2$ (NEN calcium —45 NEZ-013) in 100 μL of 0.9% saline, subcutaneously, on day 18 of gestation. The rats are sacrificed the following day by $CO_2$ asphyxiation. The fetuses are removed and the right forelimbs excised and placed in a Petri dish containing ice cold explant medium consisting of modified $BGJ_b$-Fitton Jackson media (custom formulation, Gibco No. 78-0088) adjusted to pH 7.3 to which 10 mM TES is added. The modified $BGJ_b$ media is obtained without salts, glucose or bicarbonate and is supplemented before use with 0.1 mM $MgCl_2$, 1.25 mM $CaCl_2$, 5.3 mM KCl, 0.7 mM $MgSO_4$, 130 mM NaCl, 1.0 mM $NaH_2PO_4$, 1 g/L glucose, 50 mg/L Na acetate and 100 U/mL penicillin G. The medium is sterilized by passage through a 0.2 μM filter (Nalge). Under a dissecting microscope, the bones are gently cleaned of adherent tissue and the cartilaginous ends removed.

Incubation and Drug Treatment

The midshafts are placed, individually, on 3×3 mm squares of filter paper (Gelman GN-6 metricel filters; 0.45 μM pore size) which rest on stainless steel screens in wells of 24-well culture plates containing 0.5 mL of preincubation medium. The preincubation medium is brought to 37° C. prior to transfer of bones. The preincubation medium consists of the modified $BGJ_b$ medium (with salts and glucose as above), pH 7.3, containing 29 mM $NaHCO_3$. After incubation for 18-24 hours at 37° C. in 5% $CO_2$, the bones are transferred on their screen/filter paper supports to new plates containing, in a total volume of 0.5 mL/well at 37° C., the test compound diluted in preincubation medium supplemented with 15% heat inactivated horse serum (Gibco No. 230-6050), pH 7.3, with or without a bone resorption stimulating agent (e.g. parathyroid hormone [PTH] or interleukin-1 [IL-1]). For compounds that require nonaqueous solvents, dilutions are made from the appropriate stock solution with medium. In these instances, basal and bone resorption stimulated controls exposed to an equivalent concentration of the vehicle are included. An additional group of bones that have been subjected to boiling for 1 hour (kill control) are used to establish background, non cell mediated, exchange of $^{45}Ca$. The right ulna and radius from each fetus are used. Both bones are subjected to the same treatment and each treatment group consists of bones from 4 or more fetuses. Treatments are randomly assigned using a preclinical statistics program (PS-ALLOC). After a 48 hour incubation at 37° C. in 5% $CO_2$, the bones are removed from the medium and extracted in 0.5 mL of 0.1N HCl for 1 or more days. Duplicate 150 μL aliquots of the incubation medium and the bone extract are analyzed for $^{45}Ca$ radioactivity in 5 mL of liquid scintillation cocktail.

CALCULATIONS

The percentage of bone $^{45}Ca$ released into the medium is determined as follows:

$$\frac{^{45}Ca \text{ CPM in medium}}{^{45}Ca \text{ CPM in medium} + ^{45}Ca \text{ CPM in bone}} \times 100$$

Results are normally expressed as the ratio of the percent $^{45}Ca$ release of the experimental group versus the appropriate vehicle control.

The results of this assay are set forth in TABLE 1 under the heading PTH Induced.

The useful osteoporotic activity of the compounds of formula (I) are further demonstrated by the test designated: *Basal Bone Resorption Assay:* $^{45}Ca$ Release from Rat Limb Bones.

The purpose of this assay is to test stimulators and inhibitors of bone resorption in vitro. The release of $^{45}Ca$ from in vitro labeled murine bone explants into the culture media is taken as an index of bone resorption.

Bone Labelling Procedure

Rat pups are labelled in vitro by injecting pregnant dams (18 days) with 100 μCi of $^{45}Ca$.

Explant Preparation

Two days after the initiation of labelling, the dam is anesthetized with halothane and killed by cervical dislocation. The pups are ablated and quickly decapitated. The calvaria (frontal and parietal bones), forelimbs (containing radii and ulnae), and hind limbs (tibiae) are removed and placed in control media in a petri dish. Bones are debrided of soft tissue by a combination of blunt dissection, and gentle rolling on bibulous paper, taking care not to disturb the periosteum.

Cartilaginous ends are cut off long bones. Calvaria are cut in half along midline suture. Bones are separated into 3 categories: calvaria halves, Tibiae and ulnae/radii. Groups of eight (per bone group) are randomly placed in 24-well culture plates containing 0.5 mL of control media. Cultures are maintained at 37° C. in a humidified incubator of 95% air: 5% $CO_2$.

These bones are incubated for 24 hours, media is aspirated from the bones and replaced with fresh media containing test substances. Each bone group has a control group of 8 and a dead bone group of 8. The devitalized cultures are obtained by heating the bones in medium at 55° C. for 60 minutes. The bones are incubated at 37° C. for an additional 72 hours. At the end of this period a 100 microliter aliquot of media is removed and placed in a scintillation vial. Ten mL of Aquasol is added, the $^{45}Ca$ is quantified in a scintillation spectrometer. Bones are rinsed in saline, placed in a scintillation vial, hydrolyzed overnight in 0.75 mL 6N HCl at room temperature. The hydrolyzed bone solution is neutralized by the addition of 2.25 mL of 2N NaOH, followed by 10 mL of Aquasol, the $^{45}Ca$ content is determined by scintillation spectrometry.

Analysis: $^{45}Ca$ release into culture medium from the 24-96 hour period is individually compared to $^{45}Ca$ release in control cultures and to devitalized bone via Dunnett's test. Results are expressed in TABLE 1 under the heading Basal.

The useful osteoporotic activity of the compounds of formula (I) are further demonstrated by the test designated: *Denervation Induced Osteopenia in Rats.*

The purpose of this assay is to evaluate the effect, in rats, of agents on the reduction in bone mass (osteopenia) induced by immobilization resulting from surgical severance (denervation) of the sciatic nerve.

Female, Sprague Dawley CD ® rats, ovariectomized or intact, weighing 225 to 250 g, obtained from Charles River are used.

The animals are housed in plastic cages (4 or 5 rats/cage) with food (rat purina 500 chow) and water ad libitum; 14/10 day/night cycle.

After one week of in-house acclimatization, the animals are randomly divided into groups of 6 to 10 rats/group. Each rat is weighed, anesthetized with an intraperitoneal administration of 100 mg/kg ketamine (Bristol Laboratories, Syracuse, N.Y.) and 0.75 mg/kg Acepromazine (Aveco, Ft. Dodge IA). The left hind limb is shaved and denervated by making a lateral incision parallel to the femur and by surgically removing half of a centimeter of the sciatic nerve adjacent to caudofemoralis and adductor brevis muscles. The incision is closed with wound clips. After surgery, the rats are housed in cages with absorbent bedding to minimize additional trauma to the immobilized limb. A 24 hour post-surgery recovery period is allowed before the initiation of the drug treatment.

The concentration of the drug stock is calculated to be delivered in a volume of 0.1 mL/100 gram body weight. The drug solution or a uniform suspension is prepared in 1% Tween 80 in normal saline. The drugs are administered via oral or parenteral routes daily (five times a week) for four weeks.

A sequential triple labeling of mineralized tissue is employed to determine the osseous changes (especially the bone formation) and the mineralization rates. Each animal is administered 90 mg/kg Xylenol orange (Fisher Scientific Company), S.C., 15 mg/kg Calcein (Sigma Chemical Company), S.C. and 15 mg/kg Demeclocycline (Sigma Chemical Company), i.p., approximately 21 days, 10 days and 2 days prior to the termination of the study, respectively.

At the end of the fourth week, each rat is weighed, anesthetized with an intraperitoneal administration of 100 mg/kg ketamine with 0.75 mg/kg Acepromazine and approximately 4 mL of blood collected via cardiac puncture. The anesthetized rats are euthanized by exposure to carbon dioxide. The femora and tibiae from both limbs are dissected free of soft tissue.

(i) Femora are ashed at ~1100° C. for 16 hours using a muffle furnace. —(ii) Proximal tibia are fixed, dehydrated and embedded undecalcified in a methyl methacrylate-glycol methacrylate mixture. Longitudinal tissue sections (10 microns) are prepared on a Polycut S microtome (Reichert). Staining is performed on free-floating sections using a modified Goldner's stain, which are then mounted and coverslipped.

Cancellous bone content in the proximal tibia is quantified (as two dimensional bone mineral area [B.Ar]) with an image analysis processing device (software developed by Drexel University).

The areas of the tibia selected for cancellous bone content evaluation are the primary and secondary sponiosa. To select and standardize this area for evaluation, the epiphyseal growth plate-metaphyseal junction is oriented parallel to the abscissa of the digitizing screen. Bone elements 1.7 mm (secondary spongiosa) and 0.2 mm (primary spongiosa) from the growth plate and equidistant from the flanking cortical elements are then quantified as described above. The total area evaluated is 2.30 mm wide and 1.45 mm deep, constituting a 3.34 mm² area.

Body weight, femur mass (dried or ashed) and trabecular (cancellous) bone mineral area (B.Ar) are determined.

The difference (both absolute and percent change) in femur mass and bone mineral area between intact (control) and denervated limbs of a treatment group are compared with that for the vehicle group using a one-way analysis of variance with Dunnett's test, or other multiple comparison methods.

The results are reported in Table I and II under the heading In Vivo.

Biological Test Results of Imidazo[4,5-c]Pyridines

| Ex | Y | Inhibition of Bone Resorption PTH Induced | Disuse Osteoporosis |
|----|---|---|---|
| 3 | S—⟨Ph⟩—O—C(=O)—⟨Ph⟩ | $IC_{50}$ = 32 ug/mL | 36.2% protect @ 50 mg/kg p.o. active |
| 4 | O↑S—⟨Ph⟩—O—C(=O)—⟨Ph⟩ | $IC_{50}$ = 2.31 ug/mL | |
| 5 | O↑S—⟨Ph⟩—OH | | Inactive @ 25 mg/kg p.o. |
| 8 | S—⟨Ph(OCH₃)⟩—O—C(=O)—⟨Ph⟩ | | 28% protect @ 50 mg/kg p.o. active |
| 9 | O↑S—⟨Ph(OCH₃)⟩—O—C(=O)—⟨Ph⟩ | $IC_{50}$ = 4.3 ug/mL | Inactive @ 50 mg/kg p.o. |
| 12 | S—⟨Ph⟩—(O—C(=O)—⟨Ph⟩)₂ | inactive @ 10 ug/mL | 14.5% protect @ 50 mg/kg p.o. active |
| 15 | S—⟨Ph⟩—O—C(=O)—⟨Ph(OCH₃)⟩ | inactive @ 5 ug/mL | Inactive @ 50 mg/kg p.o. |
| 16 | O↑S—⟨Ph⟩—O—C(=O)—⟨Ph(OCH₃)⟩ | $IC_{50}$ = 7.7 ug/mL | 19% protect @ 50 mg/kg p.o. active |
| 19 | S—⟨Ph⟩—C(=O)—O—⟨Ph⟩ | inactive @ 10 ug/mL | Inactive @ 50 mg/kg p.o. |
| 20 | O↑S—⟨Ph⟩—C(=O)—O—⟨Ph⟩ | active @ 10 ug/mL | 20.8% protect @ 50 mg/kg p.o. active |

Biological Test Results of Imidazo[4,5-c]Pyridines

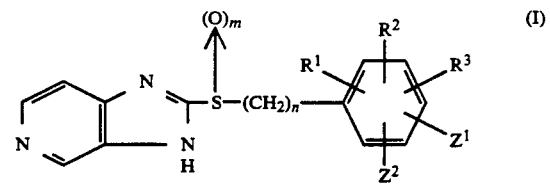

| Ex | Y | Inhibition of Bone Resorption PTH Induced | Disuse Osteoporosis |
|---|---|---|---|
| 21 | (structure) | IC$_{50}$ = 5.5 ug/mL | 27% protect @ 50 mg/kg p.o. active |
| 22 | (structure) | IC$_{50}$ > 10 ug/mL | Inactive @ 50 mg/kg p.o. |
| 25 | (structure) | IC$_{50}$ = 8.4 ug/mL | Inactive @ 50 mg/kg p.o. |
| 28 | (structure) | IC$_{50}$ = 6.2 ug/mL | 37% protect @ 50 mg/kg p.o. active |
| 31 | (structure) | Inactive @ 10 ug/mL | N.T. |
| 32 | OH (structure) | Inactive @ 10 ug/mL | Inactive @ 50 mg/kg p.o. |

Bone is degraded during the process of bone resorption and this leads to the subsequent development of osteoporosis. The present invention provides a method for the treatment of a host animal in order to modify the balance between the rate of bone resorption and the rate of bone deposition in said host animal whereby the ratio of said rate of bone resorption to said rate of bone deposition is reduced, comprising administering to said host animal an amount, sufficient to modify said balance and reduce said ratio, of 2-substituted-imidazo[4,5-c]pyridines. 2-Substituted-imidazo[4,5-c]pyridines would be administered to humans at a daily dose of 200 mg to 1200 mg.

The administration of 2-substituted-imidazo[4,5-c]pyridines in accordance with this invention can be supplemental to other regimens for the treatment of osteoporosis or periodontitis. For example, the administration of 2-substituted-imidazo[4,5-c]pyridines can be supplemental to the 600 mg to 1200 mg daily intake of calcium as calcium phosphate or calcium carbonate. Also, the administration of 2-substituted-imidazo[4,5-c]pyridines can be supplemental to estrogen replacement therapy such as 0.625 mg daily of conjugated equine estrogen.

We claim:

1. The compounds of formula (I)

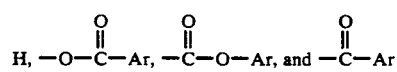

wherein $R^1$, $R^2$ and $R^3$ are independently selected from the group consisting of hydrogen, lower alkyl containing 1 to 6 carbon atoms, hydroxy, lower alkyloxy containing 1 to 6 carbon atoms, halogen, trifluoromethyl, trifluoromethoxy, nitro, cyano, phenoxy, benzyloxy, aminoacetyl, —S(O)$_p$—CH$_3$ or any two adjacent groups are joined to form methylenedioxy; $Z^1$ and $Z^2$ are independently selected from the group consisting of $$H, \quad -O-\overset{O}{\underset{\|}{C}}-Ar, \quad -\overset{O}{\underset{\|}{C}}-O-Ar, \text{ and } -\overset{O}{\underset{\|}{C}}-Ar$$

wherein Ar is phenyl; alkyl, alkoxy or hydroxy substituted phenyl; or thienyl, wherein alkyl and alkoxy contain 1 to 6 carbon atoms with the proviso that $Z^1$ and $Z^2$ are not both hydrogen; m is 0 to 2; n is 1 to 3; p is 0 to 2, and the pharmaceutically acceptable salts and hydrates thereof.

2. The compounds of formula (II)

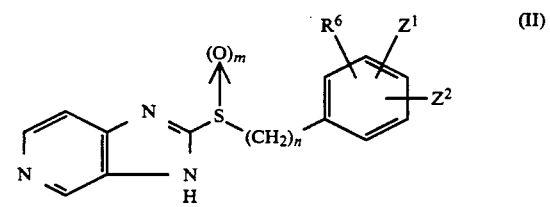

wherein $R^6$ is hydrogen, hydroxy, lower alkyloxy containing 1 to 6 carbon atoms; $Z^1$ and $Z^2$ are independently selected from the group consisting of

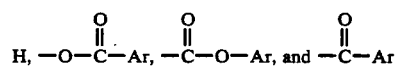

wherein Ar is phenyl; alkyl, alkoxy or hydroxy substituted phenyl; or thienyl, wherein alkyl and alkoxy contain 1 to 6 carbon atoms with the proviso that $Z^1$ and $Z^2$ are not both hydrogen; m is 0 to 2; n is 1 to 2, and the pharmaceutically acceptable salts and hydrates thereof.

3. The compound according to claim 2 wherein $R^6$ is hydrogen, hydroxy, methoxy; $Z^1$ and $Z^2$ are independently selected from the group consisting of

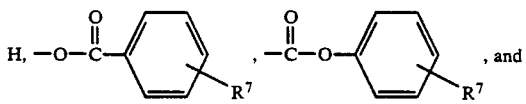

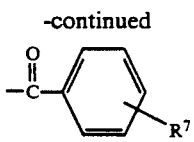

wherein R[7] is hydrogen, hydroxy, methoxy with the proviso that Z[1] and Z[2] are not both hydrogen; m is 0 to 2; and the pharmaceutically acceptable salts and hydrates thereof.

4. The compound according to claim 3 which is 3-[(1H-imidazo[4,5-c]pyridin-2-ylthio)methyl]phenol benzoate (ester) and the pharmaceutically acceptable salts and hydrates thereof.

5. The compound according to claim 3 which is 3-[(1H-imidazo[4,5-c]pyridin-2-ylsulfinyl)methyl]phenol benzoate (ester) and the pharmaceutically acceptable salts and hydrates thereof.

6. The compound according to claim 3 which is 4-[(1H-imidazo[4,5-c]pyridin-2-ylthio)methyl]-2-methoxyphenol benzoate (ester) and the pharmaceutically acceptable salts and hydrates thereof.

7. The compound according to claim 3 which is 4-[(1H-imidazo[4,5-c]pyridin-2-ylsulfinyl)methyl]-2-methoxyphenyl benzoate (ester) and the pharmaceutically acceptable salts and hydrates thereof.

8. The compound according to claim 3 which is 4-(3H-imidazo[4,5-c]pyridin-2-ylthiomethyl)benzene-1,2-diol dibenzoate (ester) and the pharmaceutically acceptable salts and hydrates thereof.

9. The compound according to claim 3 which is 3-methoxybenzoic acid 3-(1H-imidazo[4,5-c]pyridin-2-ylthiomethyl)-phenyl ester and the pharmaceutically acceptable salts and hydrates thereof.

10. The compound according to claim 3 which is 3-methoxy-benzoic acid 3-(1H-imidazo[4,5-c]pyridine-2-sulfinylmethyl)-phenyl ester and the pharmaceutically acceptable salts and hydrates thereof.

11. The compound according to claim 3 which is 3-(1H-imidazo[4,5-c]pyridin-2-ylthiomethyl)-benzoic acid phenyl ester and the pharmaceutically acceptable salts and hydrates thereof.

12. The compound according to claim 3 which is 3-(1H-imidazo[4,5-c]pyridine-2-sulfinylmethyl)-benzoic acid phenyl ester and the pharmaceutically acceptable salts and hydrates thereof.

13. The compound according to claim 3 which is [3-(1H-imidazo[4,5-c]pyridin-2-ylthiomethyl)-phenyl]-phenyl methanone and the pharmaceutically acceptable salts and hydrates thereof.

14. The compound according to claim 3 which is [3-(1H-imidazo[4,5-c]pyridine-2-sulfinylmethyl)-phenyl]-phenyl-methanone and the pharmaceutically acceptable salts and hydrates thereof.

15. The compound according to claim 3 which is 2-[(1H-imidazo[4,5-c]pyridin-2-ylthio)methyl]phenol benzoate (ester) and the pharmaceutically acceptable salts and hydrates thereof.

16. The compound according to claim 3 which is 4-[(1H-imidazo[4,5-c]pyridin-2-ylthio)methyl]-phenol benzoate (ester) and the pharmaceutically acceptable salts and hydrates thereof.

17. The compound according to claim 3 which is 5-(3H-imidazo[4,5-c]pyridin-2-ylthiomethyl)benzene-1,3-diol dibenzoate (ester) and the pharmaceutically acceptable salts and hydrates thereof.

18. The compound according to claim 3 which is benzoic acid 3-hydroxy-5-(1H-imidazo[4,5-c]pyridin-2-ylthiomethyl)phenyl ester and the pharmaceutically acceptable salts and hydrates thereof.

19. A pharmaceutical composition useful for modifying the balance between the rate of bone resorption and the rate of bone formation in a host animal whereby the ratio of said rate of bone resorption to said rate of bone formation is reduced, comprising a compound of formula (I) and a pharmaceutically acceptable carrier.

20. A method for the treatment of a host animal in order to modify the balance between the rate of bone resorption and the rate of bone formation in said host animal whereby the ratio of said rate of bone resorption to said rate of bone formation is reduced, comprising administering to said host animal an amount of a compound of formula (I) sufficient to modify said balance and reduce said ratio.

* * * * *